United States Patent
Gago Guillan et al.

(10) Patent No.: US 12,290,601 B2
(45) Date of Patent: May 6, 2025

(54) PHARMACEUTICAL COMPOSITION COMPRISING AXITINIB

(71) Applicant: Synthon B.V., Nijmegen (NL)

(72) Inventors: Manuel Gago Guillan, Sant Boi de Llobregat (ES); Rohit Kumar, Sant Boi de Llobregat (ES); Lisardo Alvarez Fernandez, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 619 days.

(21) Appl. No.: 17/609,545

(22) PCT Filed: May 8, 2020

(86) PCT No.: PCT/EP2020/062840
§ 371 (c)(1),
(2) Date: Nov. 8, 2021

(87) PCT Pub. No.: WO2020/225413
PCT Pub. Date: Nov. 12, 2020

(65) Prior Publication Data
US 2022/0226246 A1    Jul. 21, 2022

(30) Foreign Application Priority Data
May 9, 2019 (EP) .................................. 19173671

(51) Int. Cl.
| *A61K 9/20* | (2006.01) |
| *A61K 9/28* | (2006.01) |
| *A61K 31/4439* | (2006.01) |
| *A61P 35/00* | (2006.01) |

(52) U.S. Cl.
CPC .............. *A61K 9/20* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 9/28* (2013.01); *A61K 31/4439* (2013.01); *A61P 35/00* (2018.01)

(58) Field of Classification Search
None
See application file for complete search history.

(56) References Cited

U.S. PATENT DOCUMENTS

2014/0248347 A1 * 9/2014 Gierer .................. A61K 9/2054
546/256

FOREIGN PATENT DOCUMENTS

| CZ | 2018-150 | * | 4/2019 | .............. A61K 9/20 |
| CZ | 2018150 A3 | | 4/2019 | |
| WO | WO0102369 A2 | | 1/2001 | |
| WO | WO2006048751 A1 | | 5/2006 | |
| WO | WO2008122858 A2 | | 10/2008 | |
| WO | WO2013046133 A1 | | 4/2013 | |

* cited by examiner

*Primary Examiner* — Brian Gulledge
(74) *Attorney, Agent, or Firm* — Buscher Patent PLLC

(57) ABSTRACT

The present invention relates to an immediate release tablet composition comprising axitinib form IV characterized by an XRPD pattern comprising the peaks at about 8.9, 12.0, 14.6, 15.2, 15.7, 17.8, 19.1, 20.6, 21.6, 23.2, 24.2, 24.9, 26.1 and 27.5±0.1 degrees 2θ, when measured with Cu Kα1 radiation and one or more pharmaceutically acceptable excipients, wherein the composition exhibits a dissolution rate between 40% and 70% in 30 minutes when tested in 900 ml 0.01 N hydrochloric acid pH 2.0 at 37° C., 75 rpm in a USP apparatus II.

8 Claims, 2 Drawing Sheets

PHARMACEUTICAL COMPOSITION COMPRISING AXITINIB

FIELD OF THE INVENTION

The present invention relates to pharmaceutical immediate release tablet composition comprising axitinib form IV.

BACKGROUND OF THE PRESENT INVENTION

Axitinib or N-methyl-2-({3-[(E)-2-pyridin-2-ylethenyl]-1H-indazol-6-yl}sulfanyl)benzamide of the formula:

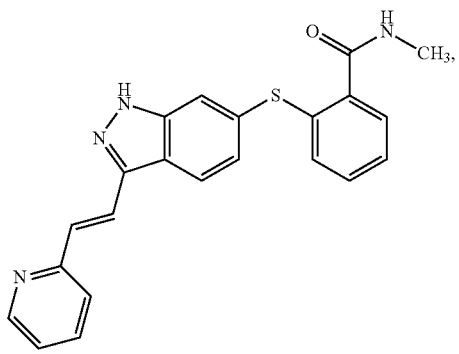 [SMILES: CNC(=O)c1ccccc1Sc1ccc2c(/C=C/c3ccccn3)n[nH]c2c1]

is an inhibitor of several tyrosine kinases involved in angiogenesis, particularly of VEGFR tyrosine kinases.

Axitinib has demonstrated clinical activity, both alone and in combination with other chemotherapeutics, in several types of tumors, including non-small cell lung cancer (NSCLC), metastatic renal cell carcinoma (mRCC), metastatic breast cancer, pancreatic cancer and thyroid cancer, and clinical studies are ongoing.

Axitinib is marketed by Pfizer under the brand name Inlyta® and it has been disclosed in WO2001002369. Pharmaceutical composition comprising axitinib have been disclosed as well (e.g. WO2013046133). Inlyta® is supplied as immediate release film-coated tablets, in different strengths (1, 3, 5 and 7 mg). Several crystalline forms of axitinib characterized by different stability and solubility have been also disclosed (e.g. WO2006048751, WO2008122858).

During formulation development for axitinib form IV, it was found that bioequivalence with the marketed product Inlyta® presented unusual difficulties. Although a prototype comprising axitinib form IV showed a dissolution profile similar to Inlyta® using FDA dissolution method, this prototype showed higher bioavailability than Inlyta® in vivo and therefore no bioequivalence to Inlyta®.

Hence, it would be desirable to have a tablet composition comprising axitinib form IV that is stable, suitable for production on commercial scale and that exhibits adequate dissolution and is bioequivalent to Inlyta®.

BRIEF DESCRIPTION OF THE PRESENT INVENTION

The present invention is based on the discovery that an immediate release tablet composition comprising axitinib form IV is bioequivalent to Inlyta® when it exhibits a dissolution rate between 40% and 70% in 30 minutes when tested in 900 ml 0.01 N hydrochloric acid pH 2.0 at 37° C., 75 rpm in a USP apparatus II.

Accordingly, the present invention provides an immediate release tablet composition comprising axitinib form IV characterized by an XRPD pattern comprising the peaks at about 8.9, 12.0, 14.6, 15.2, 15.7, 17.8, 19.1, 20.6, 21.6, 23.2, 24.2, 24.9, 26.1 and 27.5±0.1 degrees 2θ, when measured with Cu Kα1 radiation and one or more pharmaceutically acceptable excipients, wherein the composition exhibits a dissolution rate between 40% and 70% in 30 minutes when tested in 900 ml 0.01 N hydrochloric acid pH 2.0 at 37° C., 75 rpm in a USP apparatus II.

DETAILED DESCRIPTION OF THE PRESENT INVENTION

The present invention relates to an immediate release tablet composition comprising axitinib form IV characterized by an XRPD pattern comprising the peaks at about 8.9, 12.0, 14.6, 15.2, 15.7, 17.8, 19.1, 20.6, 21.6, 23.2, 24.2, 24.9, 26.1 and 27.5±0.1 degrees 2θ, when measured with Cu Kα1 radiation and one or more pharmaceutically acceptable excipients, wherein the composition exhibits a dissolution rate between 40% and 70% in 30 minutes when tested in 900 ml 0.01 N hydrochloric acid pH 2.0 at 37° C., 75 rpm in a USP apparatus II.

Axitinib is a BCS class II compound so it exhibits low solubility; it is highly soluble only in the gastric at pH 1.7. Inlyta® contains the crystalline axitinib form XLI (see CHMP assessment report of the European Medicines Agency). Form XLI is the most thermodynamically stable polymorphic form.

Other forms of axitinib have been disclosed in the prior art. The immediate release tablet of the present invention comprises axitinib form IV which is less photo-stable compared to crystalline axitinib form XLI but shows 2-3 fold higher aqueous solubility.

Figure 1:
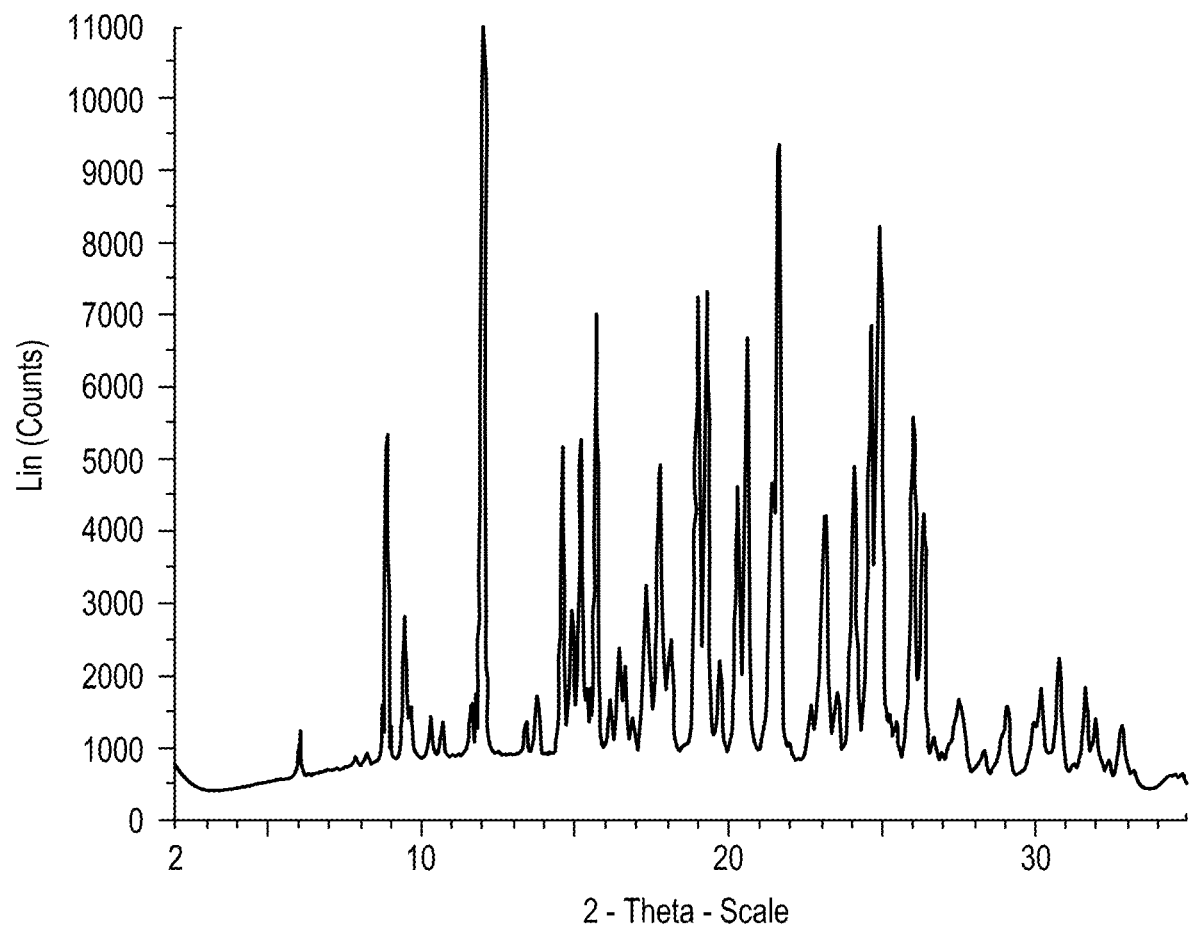
FIG. 1 shows the full XRPD pattern of axitinib form IV. For measurement conditions see the Examples section.
Figure 2:
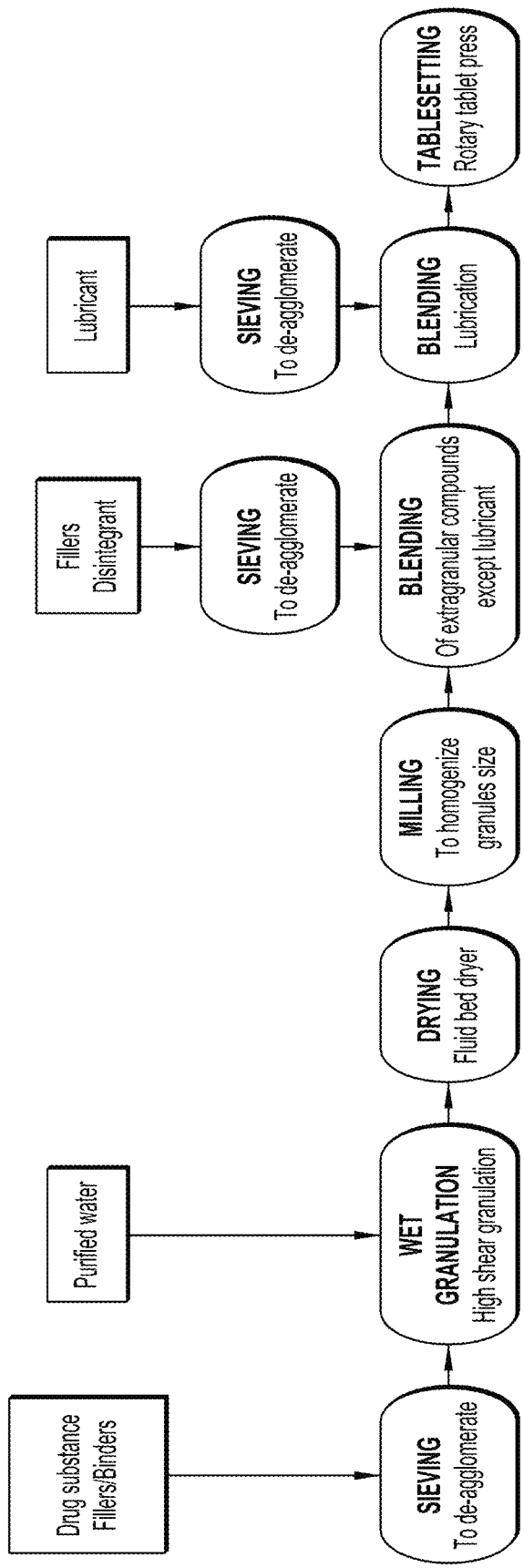
FIG. 2 shows the flow chart of the process of wet granulation applied to prepare the tablets of Example 1.

The XRPD pattern of axitinib form IV is shown in FIG. 1. The XRPD pattern comprises the peaks at about 8.9, 12.0, 14.6, 15.2, 15.7, 17.8, 19.1, 20.6, 21.6, 23.2, 24.2, 24.9, 26.1 and 27.5±0.1 degrees 2θ, when measured with Cu Kα1 radiation. The XRPD pattern of axitinib form IV may further comprise characteristic peaks at the following 2 theta (±0.1) angles: 9.5, 14.9, 16.5, 17.3, 19.3, 20.3, 24.6 and 26.4, measured using a Cu Kα1 radiation.

It is known that different polymorphic forms influence the stability, dissolution and bioequivalence of a drug product but problems were faced when axitinib form IV was used to prepare an immediate release tablet composition probably due to the higher solubility of axitinib form IV compared to form XLI. In particular, a prototype comprising axitinib form IV showed a dissolution profile similar to Inlyta® using the dissolution method as described in the FDA database (USP II (paddles), 75 rpm, 900 ml HCl 0.01N), but it showed much higher bioavailability and no bioequivalence to Inlyta®.

It was surprisingly found by the present inventors that an immediate release tablet composition comprising axitinib form IV and one or more pharmaceutically acceptable excipients exhibiting a dissolution rate between 40% and 70%, preferably the dissolution rate is between 45% and 65% in 30 minutes when tested in 900 ml 0.01 N hydrochloric acid pH 2.0 at 37° C., 75 rpm in a USP apparatus II is bioequivalent to Inlyta®.

The tablet composition of the present invention is very stable and even after storage at elevated temperature or increased relative humidity, does not show conversion of axitinib form IV into axitinib form XLI or in any other crystalline form of axitinib or an increase of impurities.

The tablet composition of the present invention is an immediate release tablet composition. As used herein the term "immediate release tablet" refers to a tablet which disintegrates rapidly (within 30 minutes, preferably within 5 min) and get dissolved to release the medicament.

In the present invention, a dissolution rate above 70% cause in vivo a higher $C_{max}$ and higher $AUC_t$ values of the tablet comprising axitinib form IV compared to the $C_{max}$ and $AUC_t$ of Inlyta®.

As used herein the term "$C_{max}$" refers to the maximum plasma concentration that a drug achieves after the drug has been administered while the term "$AUC_t$" refers to the area under the plasma concentration curve from the time point of administration to the concentration at time point t.

A dissolution rate between 40% and 70% allows to have the $C_{max}$ and $AUC_t$ values of the immediate release tablet comprising axitinib form IV similar to the $C_{max}$ and $AUC_t$ of Inlyta®.

Typically, the dissolution of drugs is evaluated by dissolution methods known to the person skilled in the art. The dissolution method used in the current invention comprises dissolving axitinib drug product at 37° C. in 900 ml of hydrochloric acid 0.01 N having pH 2.0 and stirring it using a USP apparatus having paddles II and 75 rpm.

Typically, the total weight of the tablet (without coating) of the invention is between 50 and 900 mg, preferably is between 90 and 800 mg, even more preferably is 100, 300, 500 or 700 mg.

The tablet composition according to the present invention comprises axitinib in an amount of 0.5 to 5% w/w relative to the total weight of the tablet without coating.

Hence, although the load of axitinib form IV in the tablet composition of the present invention is small, the use of axitinib in a polymorphic form IV had a big impact on the bioavailability of the immediate release tablet.

The tablet composition of the invention may contain additional pharmaceutically acceptable excipients. The excipients to be used in accordance with the present invention are well-known and are those excipients which are conventionally used by the person skilled in the art. The pharmaceutically acceptable excipients may be chosen from one or more filler, binders, disintegrants, glidants or lubricant. The excipients balance the properties of axitinib form IV in the immediate release dosage forms, without interacting with axitinib form IV.

The filler to be used in accordance with the present invention may be any filler known to a person of ordinary skill in the art. Typically, the filler to be used in accordance with the present invention is lactose, sucrose, calcium carbonate, mannitol, cellulose, maltose, sorbitol, starch or a mixture thereof. Preferably is lactose monohydrate.

The binder to be used in accordance with the present invention may be any binder known to a person of ordinary skill in the art. Suitable binder is microcrystalline cellulose (MCC), sodium carboxymethylcellulose, polyvinyl pyrrolidone (PVP), copovidone, polyvinyl pyrrolidone-vinyl acetate (PVP/VA) copolymer, hydroxypropylcellulose, hydroxypropyl methylcellulose, ethyl cellulose, hypromellose or a mixture thereof. Microcrystalline cellulose is a particularly preferred binder.

Optionally a disintegrant may be used. The disintegrant may be any disintegrant known to a person of ordinary skill in the art. Suitable disintegrant to be used in accordance with the present invention is croscarmellose sodium, crospovidone, low-substituted hydroxypropylcellulose, sodium starch glycolate or a mixture thereof. Croscarmellose sodium is a particularly preferred disintegrant. The disintegrant may be placed intragranularly or extragranularly, in a preferred embodiment the formulation of the invention has the disintegrant extragranularly.

Optionally a glidant may be used in accordance with the present invention. The glidant may be any glidant known to a person of ordinary skill in the art. Colloidal silicon dioxide is a particularly preferred glidant.

The lubricant to be used in accordance with the present invention may be any lubricant known to a person of ordinary skill in the art. Magnesium stearate is a particularly preferred lubricant.

Preferably the tablet composition of the present invention comprises:

Intragranularly:
- 0.5-5% axitinib Form IV
- 25-35% w/w of one or more filler, preferably lactose
- 20-30% w/w of one or more binders, preferably MCC Extragranularly:
- 30-50% w/w of one or more binders, preferably MCC
- 0.1-10% w/w of one or more disintegrants, preferably crosscarmellose sodium
- and 0.1-10% w/w of one or more lubricants, preferably magnesium stearate,
- all relative to the total tablet weight without coating.

The inventors have discovered that for this particular embodiment the absence of disintegrant intragranularly helps to lower the $C_{max}$ and $AUC_t$ of the immediate release tablet composition comprising axitinib form IV promoting bioequivalence to Inlyta®.

The immediate release tablet composition of the invention is prepared by a wet granulation process comprising an intragranular phase and an extragranular phase. The process used is robust and cost effective. The wet granulation process is performed with a granulation solvent (wetting agent) selected from the group consisting of water, acetone, ethanol, isopropanol or a mixture thereof. Typically, water is used as wetting agent which has the advantage of being safer to deal with. The damp mass created by adding the liquid to the powder blend is granulated and dried.

The granulation process may be a low shear wet granulation process, high shear wet granulation process or a fluid bed granulation. Preferably the granulation process is high shear wet granulation.

The intragranular phase comprises axitinib form IV and one or more pharmaceutically acceptable excipients and has the function of improving the flowability properties and the uniform distribution of axitinib form IV in the formulation. Moreover, in the present invention, the intragranular phase has also the function of modulating the dissolution profiles of the tablet composition comprising axitinib form IV when prepared by wet granulation.

Typically, the extragranular phase has the function of improving the compression properties of the final blend. In the present invention, the extragranular phase do not comprise axitinib form IV.

The tablets may be optionally further coated by a film-coat. The coating serves generally for cosmetic purposes.

The coating may be selected from amongst one or more of those suitable coating materials known in the art.

The coating may be performed by applying one or more film forming polymers, with or without other pharmaceutically inert excipients, as a solution/suspension. Coating is done using any conventional coating technique known in the art, such as spray coating in a conventional coating pan or fluidized bed processor or dip coating.

The tablet composition according to the present invention is packaged in primary packaging material, e.g. blisters. The tablet composition of the present invention is preferably packaged in PVC/PE/PVDC blisters (triplex) or Alu-Alu blisters.

In one embodiment of the invention, the intragranular phase comprises axitinib, a filler and a binder.

Axitinib is in an amount of 0.5 to 5%, more preferably 0.5 to 3%, most preferably 0.5 to 1.5% w/w relative to the total weight of the tablet without coating, the filler is in an amount of 16 to 42%, more preferably 21 to 37% w/w relative to the total weight of the tablet without coating and the binder is in an amount of 0.5 to 38%, more preferably 0.5 to 33%, even more preferably 15 to 25% w/w relative to the total weight of the tablet without coating.

In a preferred embodiment of the invention, the intragranular phase comprises axitinib form IV in an amount of 0.5 to 5%, more preferably 0.5 to 3%, most preferably of 0.5 to 1.5% w/w relative to the total weight of the tablet without coating, lactose monohydrate in an amount of 16 to 42%, more preferably 21 to 37% w/w, % relative to the total weight of the tablet without coating and microcrystalline cellulose in an amount of 0.5 to 38%, more preferably 0.5 to 33% even more preferably 15 to 25 w/w relative to the total weight of the tablet without coating.

The extragranular phase of the immediate release tablet composition of the invention comprises one or more pharmaceutical excipients. The excipients to be used in accordance with the present invention are well-known and are those excipients which are conventionally used by the person skilled in the art. The pharmaceutically acceptable excipients may be chosen from, binders, disintegrants and lubricant. In a preferred embodiment of the invention, the intragranular phase comprises 30-50% w/w of one or more binders, preferably MCC, 0.1-10% w/w of one or more disintegrants, preferably crosscarmellose sodium, and 0.1-10% w/w of one or more lubricants, preferably magnesium stearate, all relative to the total tablet weight without coating.

The present invention is illustrated by the following Examples.

EXAMPLES

The full XRPD pattern of axitinib form IV of FIG. 1 was obtained using a Bruker-AXS D8 Vario diffractometer with θ/2θ geometry (reflection mode), equipped with a Lynxeye detector and applying the following measurement conditions:
Start angle (2θ): 2.0°
End angle (2θ): 35.0°
Scan step width: 0.02°
Scan step time: between 0.2-2.0 seconds
Radiation type: Cu
Radiation wavelengths: 1.5406 Å (Kα1), primary monochromator used
Exit slit: 6.0 mm
Focus slit: 0.2 mm
Divergence slit: Variable (V20)
Antiscatter slit: 11.8 mm
Receiving slit: 20.7 mm

Example 1: Pharmaceutical Composition Comprising Axitinib Form IV

The tablets comprising axitinib form IV were prepared by wet granulation process and have the composition as given in table 1.

TABLE 1

| Component | Axitinib tablet composition | |
|---|---|---|
| | mg/tablet | % |
| Intragranular components | | |
| Axitinib form IV | 7.000 | 1.00 |
| Lactose monohydrate | 224.000 | 32.00 |
| Microcrystalline cellulose | 162.750 | 23.25 |
| Extragranular components | | |
| Microcrystalline cellulose | 294.000 | 42.00 |
| Croscarmellose sodium | 7.000 | 1.00 |
| Magnesium stearate | 5.250 | 0.75 |
| Total core tablet weight | 700.0 | 100.0 |

Example 2

The composition of the example 1 is film coated with 39% HPMC, 28% lactose monohydrate, 16% titanium dioxide, 9% iron oxide red, 8% triacetin to obtain the final film coated tablet.

Example 3

The stability of the film coated tablet of example 2 in Alu-Alu has been evaluated.

| | 6 months |
|---|---|
| 40° C./75% humidity | No impurities above 0.1% |
| 25° C./60% humidity | No impurities above 0.1% |

The invention claimed is:

1. An immediate release tablet composition comprising axitinib form IV characterized by an XRPD pattern comprising the peaks at about 8.9, 12.0, 14.6, 15.2, 15.7, 17.8, 19.1, 20.6, 21.6, 23.2, 24.2, 24.9, 26.1 and 27.5±0.1 degrees 2θ, when measured with Cu Kα1 radiation and one or more pharmaceutically acceptable excipients, said tablet comprises an intragranular phase and an extragranular phase, wherein said intragranular phase consists essentially of:
 0.5-5% axitinib Form IV
 25-35% w/w of lactose, and
 20-30% w/w of microcrystalline cellulose; and
said extragranular phase comprises:
 30-50% w/w of one or more binders,
 0.1-10% w/w of one or more disintegrants, and
 0.1-10% w/w of one or more lubricants,
all relative to the total tablet weight without coating; and wherein the composition exhibits a dissolution rate between 40% and 70% in 30 minutes when tested in 900 ml 0.01 N hydrochloric acid pH 2.0 at 37° C., 75 rpm in a USP apparatus II.

2. The immediate release tablet composition according to claim 1, wherein the disintegrant is crosscarmellose sodium and the extragranular binder is microcrystalline cellulose.

3. The immediate release tablet according to claim 1 which is further film coated.

4. The immediate release tablet composition according to claim 1, which was prepared by wet granulation.

5. The immediate release tablet composition according to claim 2, wherein the extragranular phase lubricant is magnesium stearate.

6. The immediate release tablet composition according to claim 1, wherein said extragranular phase consists essentially of:
   30-50% w/w of microcrystalline cellulose,
   0.1-10% w/w of crosscarmellose sodium, and
   0.1-10% w/w of magnesium stearate,
   all relative to the total tablet weight without coating.

7. The immediate release tablet composition according to claim 6, wherein said composition exhibits a dissolution rate between 45% and 65% in 30 minutes when tested in 900 ml 0.01 N hydrochloric acid pH 2.0 at 37° C., 75 rpm in a USP apparatus II.

8. The immediate release tablet composition according to claim 1, wherein said composition exhibits a dissolution rate between 45% and 65% in 30 minutes when tested in 900 ml 0.01 N hydrochloric acid pH 2.0 at 37° C., 75 rpm in a USP apparatus II.

* * * * *